United States Patent
Shambroom et al.

(10) Patent No.: US 6,985,833 B2
(45) Date of Patent: Jan. 10, 2006

(54) SYSTEM AND METHOD FOR THE DETECTION AND REMOVAL OF RADIO FREQUENCY NOISE ARTIFACT FROM BIOPOTENTIAL SIGNALS

(75) Inventors: John R. Shambroom, Arlington, MA (US); Charles P. Smith, Medway, MA (US); Hongmei Cai, Northboro, MA (US); Edwin Merrick, Stow, MA (US)

(73) Assignee: Aspect Medical Systems, Inc., Newton, MA (US)

( * ) Notice: Subject to any disclaimer, the term of this patent is extended or adjusted under 35 U.S.C. 154(b) by 0 days.

(21) Appl. No.: 10/177,708

(22) Filed: Jun. 21, 2002

(65) Prior Publication Data

US 2003/0052775 A1 Mar. 20, 2003

Related U.S. Application Data (60) Provisional application No. 60/299,983, filed on Jun. 21, 2001.

(51) Int. Cl.
  *G08B 1/08* (2006.01)

(52) U.S. Cl. ..................................................... 702/191
(58) Field of Classification Search ................. 702/191; 340/539, 573; 359/9; 704/205, 226; 455/351, 455/296, 517, 168, 226, 208; 307/46; 429/23; 323/288; 324/248, 303; 381/4, 56; 375/143; 600/441; 73/620; 331/2; 128/660
See application file for complete search history.

(56) References Cited

U.S. PATENT DOCUMENTS

| 5,381,804 A | 1/1995 | Shambroom ................ 128/731 |
| 5,792,069 A | 8/1998 | Greenwald et al. ......... 600/544 |
| 6,067,467 A | 5/2000 | John ........................... 600/544 |
| 6,081,163 A * | 6/2000 | Ujiie et al. ..................... 331/2 |
| 2001/0000959 A1 * | 5/2001 | Campana, Jr. ........... 340/573.1 |

* cited by examiner

*Primary Examiner*—Bryan Bui
*Assistant Examiner*—Tung Lau (74) *Attorney, Agent, or Firm*—Wilmer Cutler Pickering Hale and Dorr (57) ABSTRACT

A system and method of identifying and removing artifact from radio frequency noise from biopotentials identifies epochs contaminated with radio frequency noise. Contaminated epochs are then replaced with recent uncontaminated epochs stored in a buffer, depending on the current level of artifact and the availability of suitable data. Discontinuities arising at the beginning of the replaced epochs are smoothed by means of a windowing function.

16 Claims, 8 Drawing Sheets

SYSTEM AND METHOD FOR THE DETECTION AND REMOVAL OF RADIO FREQUENCY NOISE ARTIFACT FROM BIOPOTENTIAL SIGNALS

CROSS REFERENCE TO RELATED APPLICATION

This application claims priority under 35 U.S.C. 119(e) to U.S. Provisional application Ser. No. 60/299,983, filed Jun. 21, 2001.

BACKGROUND OF THE INVENTION

Patient monitors that acquire and process electroencephalographic (EEG) signals are commonly used in surgical settings to monitor the patient's state or hypnosis and sedation. The EEG is characterized by amplitudes in the microvolt range and frequencies in the 0–50 Hz frequency band. The use of processed EEG can be impaired by radio frequency electrical noise in the operating room environment. It is common surgical practice for a surgeon to use electrosurgical devices as cutting and coagulating tools. Electrosurgical devices typically use AC voltages in the 500 KHz to 3 MHz frequency range. Typical amplitudes may be 100 to 5000 volts. The application of the electrosurgical scalpel frequently causes electrical arcing, generating wide-band electrical noise. In addition, the electrosurgical waveform may be modulated by switching it on and off at a certain duty cycle. This modulation also generates wide-band electrical noise. Electrical noise arising from electrosurgical devices are easily picked up by other monitoring devices in the operating room. Due to their large amplitude and wide-band frequency characteristics, electrosurgical devices are a major source of operating room electrical interference.

SUMMARY OF THE INVENTION

The present invention provides a system and method of identifying and removing artifact from radio frequency noise from biopotential signals. Biopotential signals are divided into epochs and epochs contaminated with radio frequency noise are identified. Epochs with radio frequency noise are replaced with epochs without such noise. In order to avoid errors in the process, each epoch must be identified by two different artifact identification techniques as containing radio frequency noise. Discontinuities arising at the beginning of replaced epochs are smoothed by means of a windowing function.

DETAILED DESCRIPTION OF THE PREFERRED EMBODIMENTS

Figure 1:
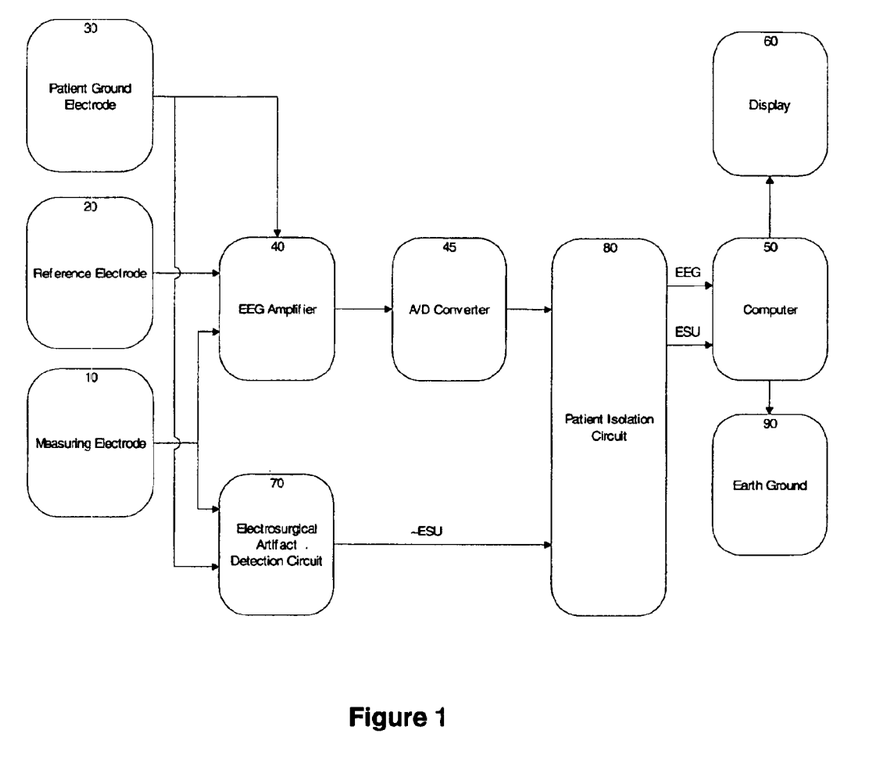
FIG. 1 is a block diagram EEG analysis with electrosurgical artifact detection.

FIG. 1 shows an electroencephalographic (EEG) analysis system. This system consists of a set of electrodes that are positioned on the head of a patient (not shown) to be monitored. Preferably at least three electrodes are used: a measuring electrode 10, a reference electrode 20 and a ground electrode 30. In a preferred embodiment the electrodes are silver/silver chloride electrodes, but any type of biopotential electrode may be used. An amplifier 40, which in a preferred embodiment is a differential amplifier, amplifies the voltage difference between the measuring electrode 10 and the reference electrode 20. This voltage difference is referred to as the EEG signal. The ground electrode 30 is connected to the amplifier ground to provide a common voltage baseline for the amplifier 40. The amplifier 40 may also filter the EEG signal obtained from the EEG electrodes 10 and 20. The output of the EEG amplifier 40, the EEG signal, is provided as an input to an analog/digital converter 45 which samples the analog output from amplifier 40 and converts it into a digital sequence for subsequent computer analysis. The amplifier 40 is isolated from earth ground 90 by a patient isolation circuit 80 to protect the patient from electric shock hazard. In the preferred embodiment patient isolation circuit 80 is a high isolation transformer. The output of the analog/digital converter 45 is provided as an input to the isolation circuit 80, and from there it is input to a computer 50. The computer 50 may optionally have a display system 60 for communicating to a clinician or technician the various metrics calculated from the amplified EEG signal. The EEG analysis system also incorporates an electrosurgical artifact detection circuit 70 that detects whenever an electrosurgical device is operating, whether the device is in actual surgical use or simply being switched into the operating mode without patient contact. The input to this circuit is the signal from the measuring electrode 10. The detection circuit 70 must also be isolated from earth ground. The output of this circuit, denoted as ~ESU, is provided as an input to the isolation circuit 80, and from there to a computer 50.

Figure 2:
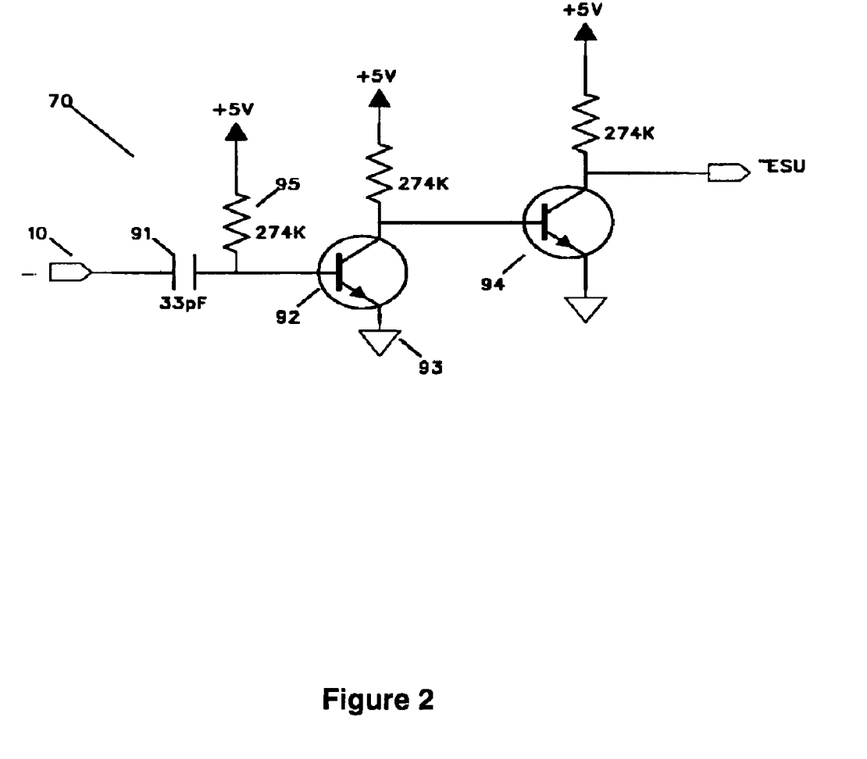
FIG. 2 is a circuit diagram of electrosurgical artifact detection circuit used in the system of FIG. 1.

Referring to FIG. 2, the electrosurgical artifact detector circuit 70 is shown. The electrosurgical artifact detector circuit 70 is sensitive to electro-surgery current passing from a patient lead or leads 10, 20, 30 through the stray capacitance of the patient isolation circuit 80 as well as other stray capacitances, to the earth ground of the bio-potential monitor enclosure. These currents constitute a common mode signal. The current is also sensitive to voltage differences between the patient measuring electrode 10 and patient ground electrode 30. These voltages constitute differential mode signals. The electrosurgical artifact detection circuit 70 is capacitively coupled to the measuring electrode lead 10 in order to provide sensitivity to high frequency interference only. In the present invention, electrosurgical artifact detection circuit 70 will detect electrosurgical artifact within a range of 100 KHz and 3 MHz. As can be seen in FIG. 2, the base of a first stage transistor, 92, is capacitively coupled through capacitor 91 to a patient lead 10 while the emitter of this transistor is connected to the local, isolated ground 93. The local, isolated ground 93 has capacitance to earth ground. A second transistor 94, is directly coupled to the first stage so as to provide an output capable of interfacing with a logic level input.

The operation of the first stage is novel in that it uses RF energy to turn off the first transistor 92. Other amplitude modulation detectors use RF current to turn on the detector.

Using the RF energy to turn off the first transistor is advantageous for this application, as there is no need to extract information from the RF being detected, it is simply the presence of RF to which this detector is designed to respond. The advantage here, is that it is possible to set a threshold current level to which the detector will respond. Since the supply voltage is regulated and the base emitter changes only 2.2 mv per degree centigrade, the base bias current is supplied from the regulated supply to the base of the first transistor 92, via a single resistor 95. In the preferred embodiment the current is approximately 20 micro-amperes. This current is fixed and varies little with temperature. Thus, the minimum sensitivity level of the detector circuit 70 is easily set by the selection of the base bias resistor 95.

The operation of the electrosurgical artifact detection circuit 70 will now be described. Transistor 92 is normally on, keeping transistor 94 off. When an electrosurgical unit generator is operated and the peak RF current through the patient leads into the detector exceeds the base bias current, transistor 92 turns off on half cycles of the RF from the electrosurgical unit generator. Any current higher than the base bias current will also cause this result. When transistor 92 turns off, transistor 94 turns on and this information is detected by a logic circuit and passed to the controller processing the data stream. Even if the output of transistor 94 is not sampled at a rate equal to or higher than the RF frequency of the electrosurgical unit there are a half million chances per second to notice that RF current is present.

In addition to detecting electrosurgical artifact by using the circuit of FIG. 2, various digital signal-processing (DSP) techniques may also be used to detect artifacts. These techniques may be designed to detect different characteristics of the electrosurgical artifact. In a preferred embodiment, the present invention uses two such DSP techniques.

Electrosurgical artifact typically contains high frequency (HF) noise. This HF noise is presumed to arise from arcing that occurs when an electrosurgical device is in close proximity, but not in contact with, grounded tissue. The dose proximity creates a spark gap, which may be jumped if the voltage difference is high enough. This high frequency noise may be continuous, lasting 30 seconds or longer. In order to detect this HF noise, the present invention examines the root mean square (RMS) power of the EEG signal for changes that are characteristic of this type of HF noise.

In the present invention, this RMS sudden change artifact-processing process is applied to one epoch of data at a time. An epoch length of one second is preferably used, and each new epoch overlaps the previous one by 50% (a new epoch every half second).

The process compares the $30^{th}$ percentile of the log RMS power values of the entire epoch of data to the maximum of log RMS power values of successive short time slices within the epoch. Epochs are marked as potentially containing artifact when the difference in log RMS power values is greater than a threshold. A software artifact flag, the Sudden Change Flag, is used to store this information. A separate artifact flag is maintained for each epoch. The $30^{th}$ percentile of the values in the long buffer is used to reduce the effect of high power noise spikes; this has the effect of ignoring the 70% of values with the highest power. This technique is effective for signals with intermittent periods of noise. However, the use of a value derived from the data means the artifact detection process will adapt to continuous high frequency noise. Thus, artifact detection will eventually fail if the high frequency noise is present in more than 70% of the epochs from which the values in the long buffer are computed. For this reason, the buffer length should be set to 1.5 times the longest expected period of continuous artifact. In the present invention, a buffer length of 1.5 minutes is used, enabling up to 1.05 minutes of artifact to be handled correctly (70% of 1.5 minutes). This process will now be described with reference to FIG. 3.

Figure 3:
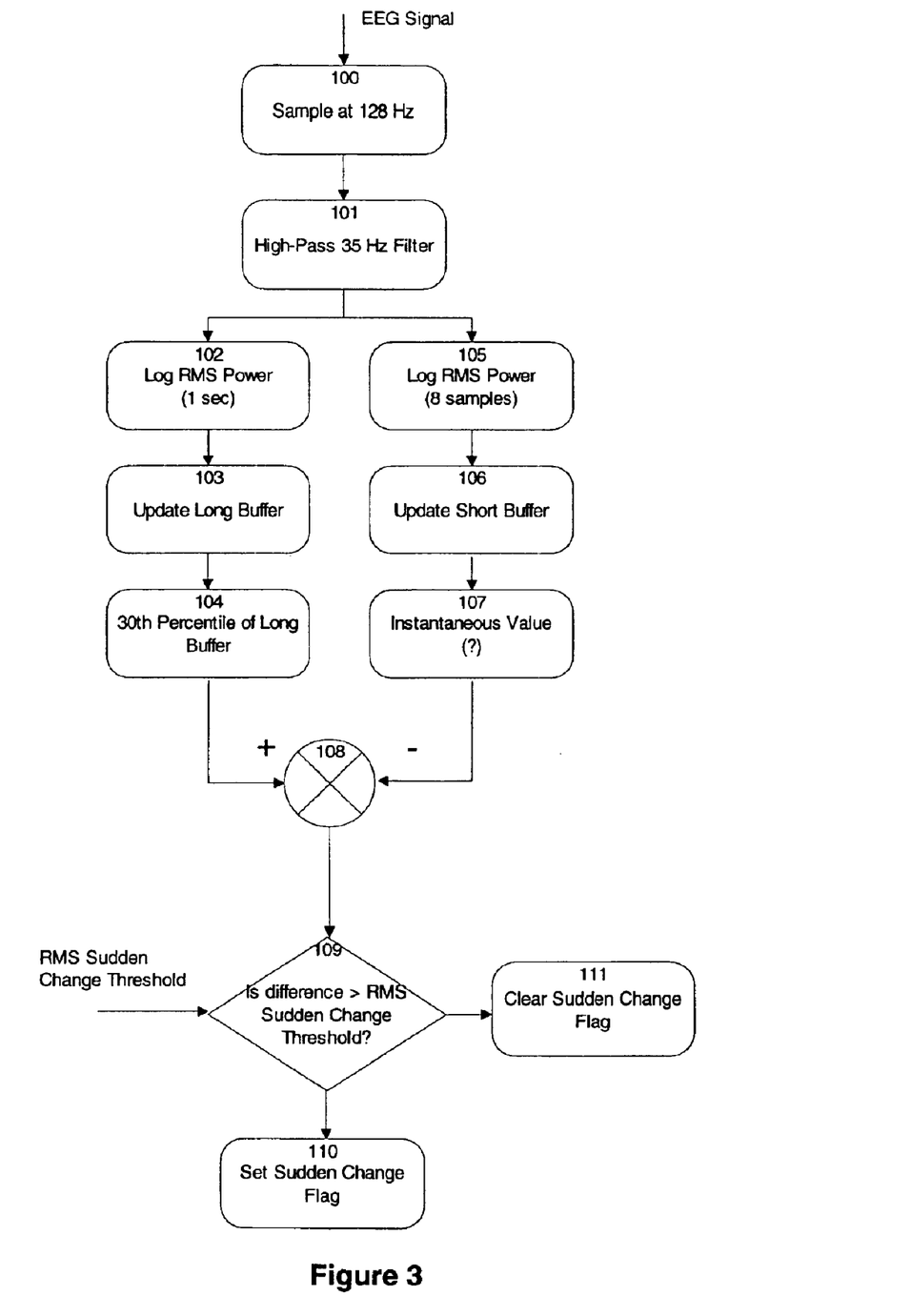
FIG. 3 is a flow chart of the steps for performing RMS sudden change of the present invention.
Figure 4:
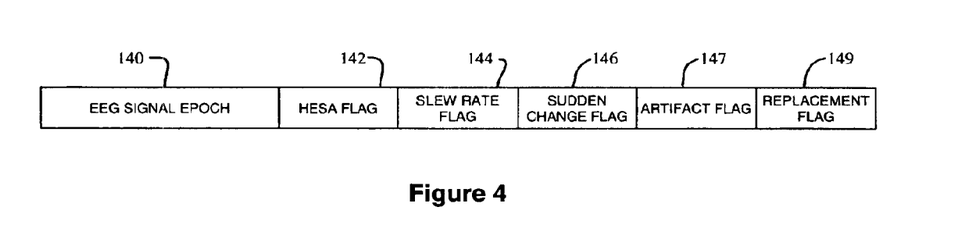
FIG. 4 is a representation of an epoch data structure used in the present invention.

In step 100 the system samples the EEG signal at 128 samples per second. The sample signal is then filtered in step 101 using a $4^{th}$ order high pass Butterworth filter with a −3 dB frequency at 35 Hz. For each epoch of sampled data, the system calculates the log of the total RMS power in step 102 and uses this value to update the long buffer in step 103. The long buffer is a first in, first out (FIFO) buffer, in which the oldest value is deleted when the newest value is added. The long buffer contains all the 1 second RMS power values from the most recent 1.5 minutes of data. For each epoch of sample data the log of the total RMS power is also calculated for each of the consecutive 8 sample periods in each epoch in step 105. In step 106, the values are stored in a second FIFO buffer. This second buffer is referred to as the short buffer and contains all the eight-sample RMS power values from the most recent 1.5 minutes of data.

In step 108 the difference between the $30^{th}$ percentile of values in the long buffer and a maximum of the values in the short buffer over the last 30 seconds is computed. This difference is compared to an RMS sudden change threshold in step 109. In preferred embodiment of the present invention, the threshold value is 0.4. The threshold is selected such that there is acceptable variance in the biologic process being measured. If the difference is greater than the sudden change threshold, a sudden change flag 146 is set for the current epoch in step 110. Otherwise the sudden change flag 146 is cleared for the current epoch in step 111.

Figure 5:
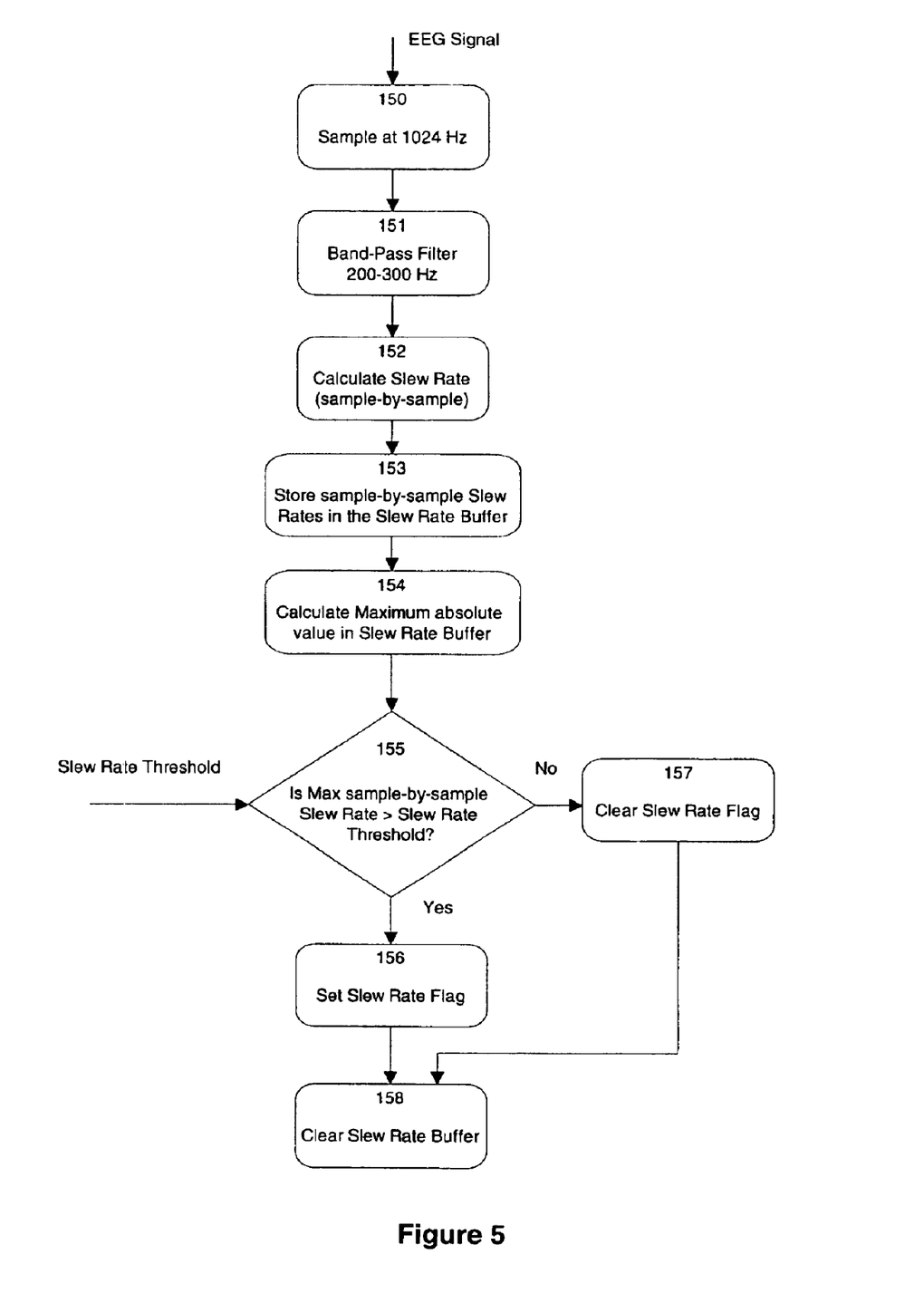
FIG. 5 is a flow chart of the steps for performing slew rate detection of the present invention.

A second method of detecting electrosurgical artifact is shown in FIG. 5. This method is based on the rate of change of the sampled data, commonly known as the slew rate. An artifact flag (the slew rate flag) is used to store this information, with a separate slew rate flag being maintained for each epoch. This method operates by first sampling the EEG signal at 1024 samples per second in step 150. In step 151, each epoch of sample data is filtered using a band pass filter. In a preferred embodiment the filters are comprised of two $4^{th}$ order Butterworth filters with one being a high pass filter with a −3 dB frequency at 200 Hz and the other being a low pass filter with a −3 dB frequency at 300 Hz. Next, in step 152, a sample-by-sample slew rate is calculated and the results for the entire epoch are stored in a buffer. In step 154 the maximum slew rate value in the buffer is calculated and then in step 155 such maximum slew rate in a current epoch is compared with a slew rate threshold, which in a preferred embodiment is 100 microvolts/sec. If the maximum slew rate exceeds the slew rate threshold, a slew rate flag 144 is set for the current epoch 140 in step 156. Otherwise, it is cleared for the current epoch in step 157. Finally, the slew rate buffers are cleared in preparation for processing the next epoch in step 158.

The method of artifact processing used in the present invention dynamically filters the EEG signal, effectively removing the electrosurgical artifact from the ongoing EEG signal. For this reason, the method of electrosurgical artifact filtering is applied only when an electrosurgical artifact is detected in a particular epoch by both the artifact detection circuit 70 and at least one of the two software detection methods. This process of electrosurgical artifact classification will now be described with reference to FIG. 6.

Figure 6:
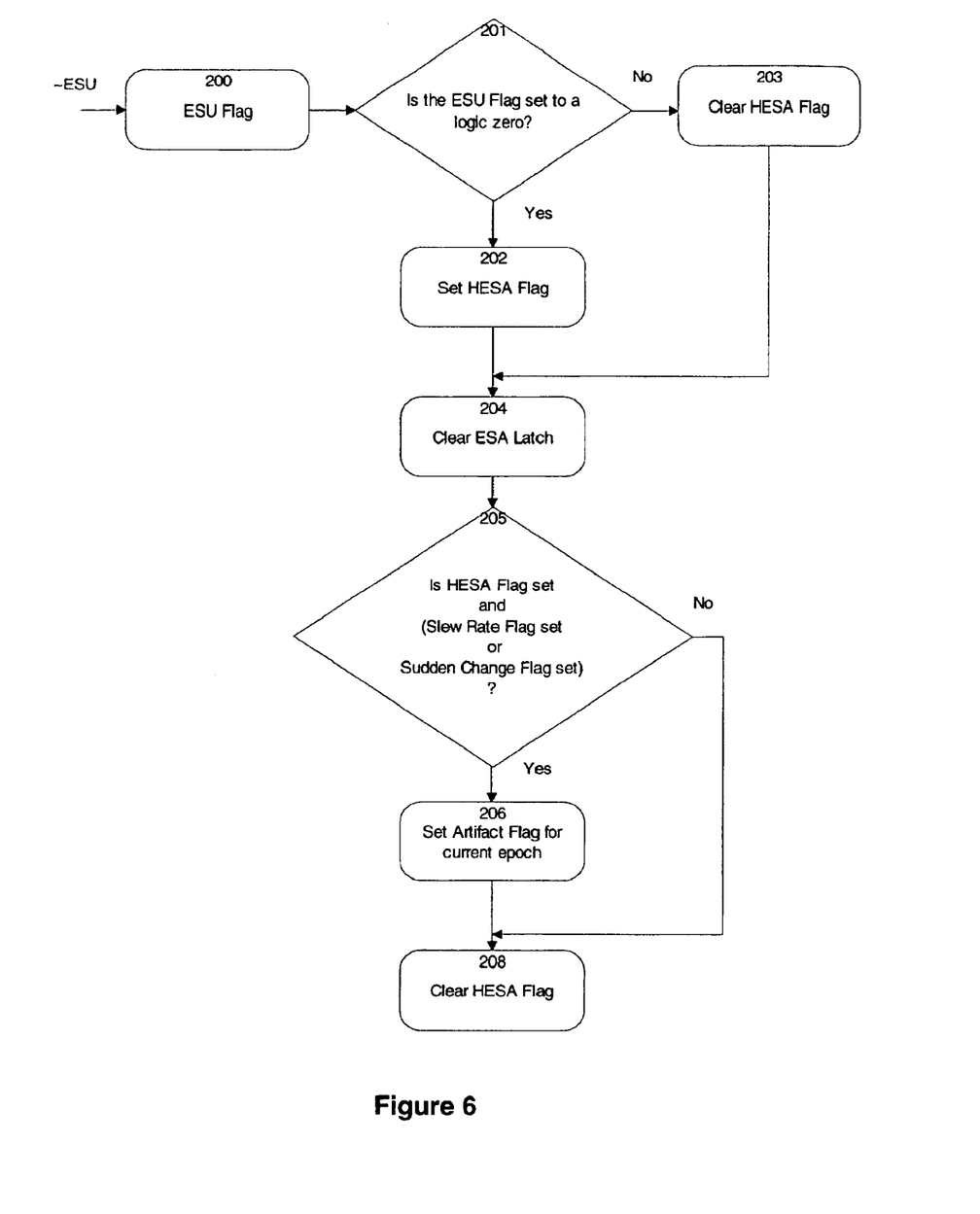
FIG. 6 is a flow chart of the steps for performing artifact classification of the present invention.

The EEG signals are typically analyzed epoch by epoch, and the present invention preferably uses an epoch length of 1 second. For this reason, it is desirable to classify the EEG as to whether or not each epoch contains electrosurgical artifact. For this reason, the output signal ~ESU is typically used to set a flag. In step 200 the ESU flag is set by the ~ESU signal output of the electrosurgical artifact detection circuit 70. After each epoch of EEG signal is acquired, the electrosurgical unit flag is examined in step 201 in order to determine whether it is set to a logic zero. If the electrosurgical unit flag is set, the hardware electrosurgical artifact (HESA) flag 142 is then set in step 202. If the electrosurgical unit flag is not set then the HESA Flag 142 is cleared in step 203. Regardless of the electrosurgical unit flag value, it is cleared in step 204 before acquisition of the next epoch begins.

In order for an epoch to be classified as containing electrosurgical artifact, the HESA flag must be set. In addition, either the slew rate flag 144 or the sudden change flag 146 must be set. If this combination of conditions is found to be met in step 205, the artifact flag 147 is set for the current epoch 140 in step 206. The HESA flag 142 is also cleared in step 208.

The essential function of the artifact-processing process is to replace epochs containing electrosurgical artifact with previously acquired artifact-free epochs. EEG is generated by cerebral activity, which in the strictest sense is a non-stationary process. However, metrics derived from the EEG using various signal processing measures such as power spectral analysis, bispectral analysis and time-domain analysis are robust to the assumption that cerebral activity is weakly stationary. For this reason error introduced into the EEG signal by replacing an artifact-contaminated epoch with an artifact-free epoch is small compared to the benefit gained from additional data as long as the epoch used for replacement is from the recent past As the age of the replacement epoch increases, so does the potential introduced error. For this reason, the age of the epoch used to replace the artifact-contaminated epoch is limited in a preferred embodiment of the present invention to no more than 1 minute.

Another means of limiting the potential error introduced by data replacement is to perform the replacement only if the proportion of epochs contaminated by artifact in the recent past is relatively large, which increases the importance of each artifact-free epoch to the final result. If artifact replacement is performed when the proportion of artifact-contaminated epochs is small, the potential increased error resulting from artifact replacement is not sufficiently outweighed by the benefit of additional data. In the present invention, whether or not artifact-contaminated epochs are replaced depends upon the prevalence of artifact of all types. The ratio of non-artifact-contaminated epochs to the total number of epochs in the last minute is called the Signal Quality Ratio (SQR). In a preferred embodiment of the present invention, an electrosurgical artifact-contaminated epoch is replaced only if the SQR is less than 50% (the electrosurgical artifact ratio threshold); that is, if more than 50% of the epochs from the last minute of data have been classified as containing artifact. If an electrosurgical artifact contaminated epoch is not replaced, it is excluded from further processing.

Two data buffers are used for the artifact-processing process. The first buffer (the EEG buffer) stores artifact-free EEG signal. The second buffer (the Flag buffer) stores the various artifact flags of the corresponding epochs in the EEG buffer as well as a pointer to the location of those epochs in the EEG buffer. The Flag buffer also stores a replacement flag, which tracks whether or not the epoch has been used for artifact replacement. Only artifact-free epochs are stored in the EEG buffer. While the methods of artifact detection described here are limited to electrosurgical artifact, in practice the artifact detection software will include detectors that are filters for a variety of different types of artifact, such as movement artifact, 60 Hz noise, base-line wander, ECG and pacer artifact, etc. The Flag buffer will contain a flag (the Artifact Flag) indicating whether any artifacts were detected in the corresponding epoch. The artifact flag will generally be set if any of the individual artifact flags are set. In order to be used as replacement data, an epoch must be completely artifact free; that is, the artifact flag must be clear (not set). Alternately, the Flag buffer may contain flags for each of the different artifacts and these may be tested individually to ascertain whether the epoch in question is free of detected artifact The memory requirements of the EEG buffer depend on the maximum age of epochs used for replacement of artifact-contaminated epochs, the electrosurgical artifact ratio threshold, the sampling rate and the data word length. A preferred embodiment of the present invention uses data no older than 1 minute for replacement and an electrosurgical artifact ratio threshold of 50%. Therefore, because neither artifact-contaminated data nor data older than one minute need be saved, the EEG buffer need only be large enough to store 30 seconds of EEG signal.

When the acquisition of a new epoch is complete, the Flag buffer is updated so that the electrosurgical artifact and artifact flags and the EEG buffer pointer corresponding to the oldest epoch is shifted out (overwritten), effectively deleting it. If the new epoch is artifact-free, the EEG buffer is also updated to ensure that the buffer contains only the most recent artifact-free epochs. The EEG signal in the EEG buffer is used only once to replace artifact-contaminated epochs.

Figure 7:
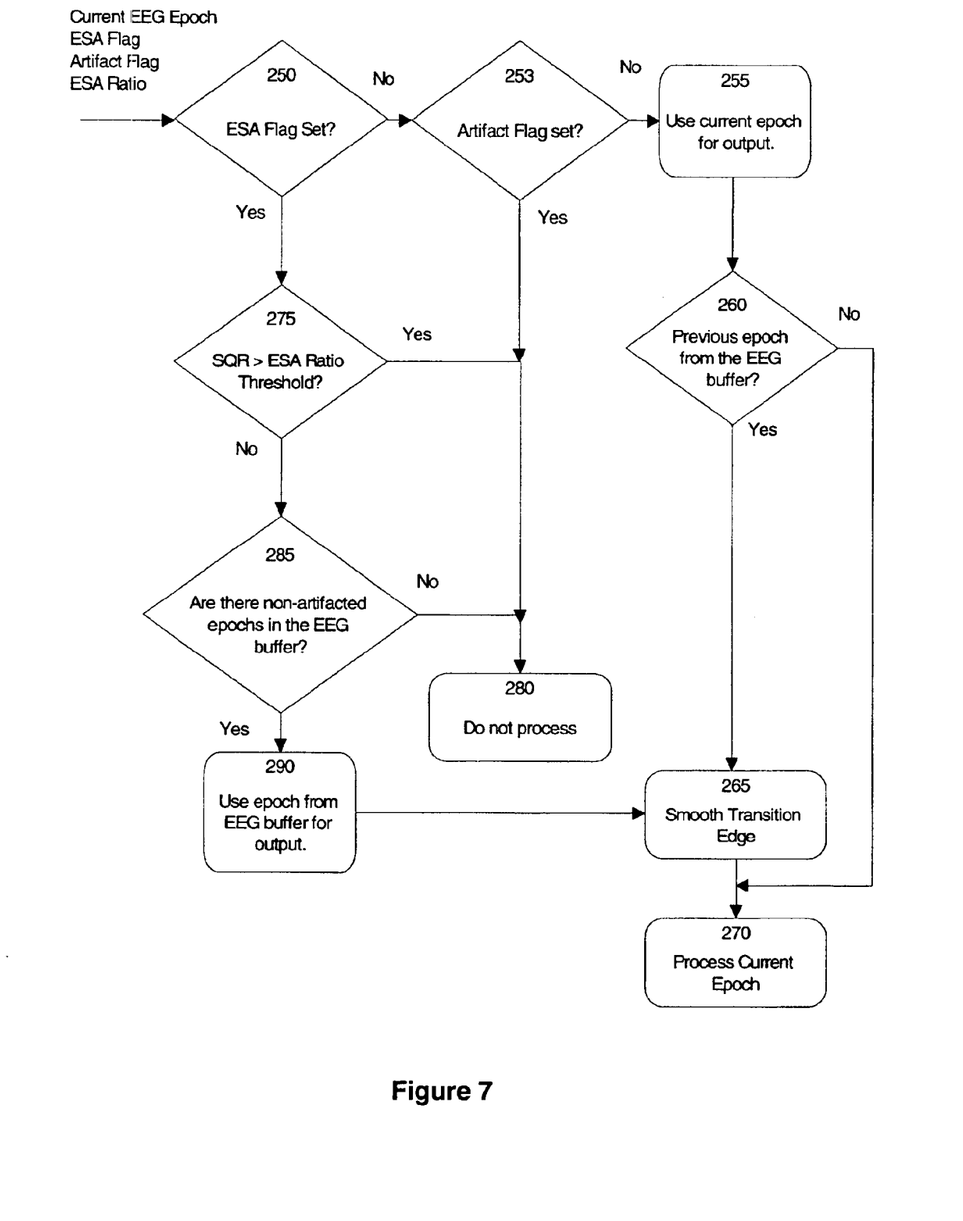
FIG. 7 is a flow chart of the steps for performing epoch replacement of the present invention.

The process for the replacement of epochs that are classified as artifact-contaminated is shown in FIG. 7. For simplicity, this discussion will be directed to electrosurgical artifact, though those skilled in the art will recognize that this invention may be used with any number of different artifact types. Artifact processing begins after acquisition of the current epoch is complete, the epoch has been classified as to its artifact status (contaminated or artifact-free, both ESA and other artifacts), and the SQR has been updated. First, the ESA flag 148 is checked to ascertain the ESA classification of the current epoch 140 in step 250. If the ESA flag 148 is not set (is clear), the current epoch 140 is free of electrosurgical artifact. If the artifact flag 147 is also not set as determined in step 253, the current epoch 140 is artifact-free and may thus be used for processing in step 255 without replacement. If the artifact flag 147 is determined to be set in step 253, the epoch 140 contains artifact other than electrosurgical artifact, and the epoch is not used for processing and is discarded in step 280. If the system determines in step 260 that the previous epoch came from the EEG buffer (i.e., it was replaced by this artifact processing process), the transition between the end of the previous epoch and the start of the current epoch is smoothed in step 265 using the process described below. The discontinuity is a result of the two epochs being non-contiguous in time. If it is determined in step 260 that the previous epoch did not come from the EEG buffer, there is no need to smooth the transition between the previous and current epoch. In either event, the current epoch, smoothed or not, is processed to derive the various EEG metrics from it in step 270. The current epoch may also be displayed on a display device as the ongoing artifact-corrected EEG signal.

If the system finds the ESA flag 148 is set in step 250, the current epoch is contaminate with electrosurgical artifact. The epoch is thus a candidate for replacement if the current level of electrosurgical artifact is high and there is data in the EEG buffer to use for replacement. To this end, the current SQR is compared against the electrosurgical artifact ratio threshold in step 275. If the SQR is greater than or equal to the electrosurgical artifact ratio threshold, the current epoch is not replaced. The current epoch is marked as artifacted so that it will be excluded from further processing in step 280. It may also be displayed on a display device as the ongoing EEG signal.

If the SQR is less than the electrosurgical artifact ratio threshold, it is next determined in step 285 whether there are epochs in the EEG buffer available for use as replacement epochs. Recall that only non-artifacted epochs are stored in the buffer. In addition, epochs may be used for replacement only once. To ascertain the replacement status of the epochs in the EEG buffer, the replacement flags in the flag buffer are checked. If there are no epochs in the EEG buffer whose corresponding replacement flags indicate that they have not been used for replacement, the current epoch is not replaced, and it will be excluded from further processing in step 280. It may also be displayed on a display device as the ongoing EEG signal.

If there is a non-artifacted epoch in the EEG buffer that has not been used for replacement and the SQR is less than the electrosurgical artifact ratio threshold, the available epoch in the EEG buffer is used to replace the current epoch in step 290. The replacement epoch is used for output and its replacement flag 149 is set to indicate that it has now been used for replacement. The transition edge between the end of the previous epoch and the beginning edge of the replacement epoch are adjusted in step 265. The adjusted replacement epoch is processed to derive the various processed EEG metrics from it in step 270. The adjusted replacement epoch may also be displayed on a display device as the ongoing artifact-corrected EEG signal.

Figure 8:
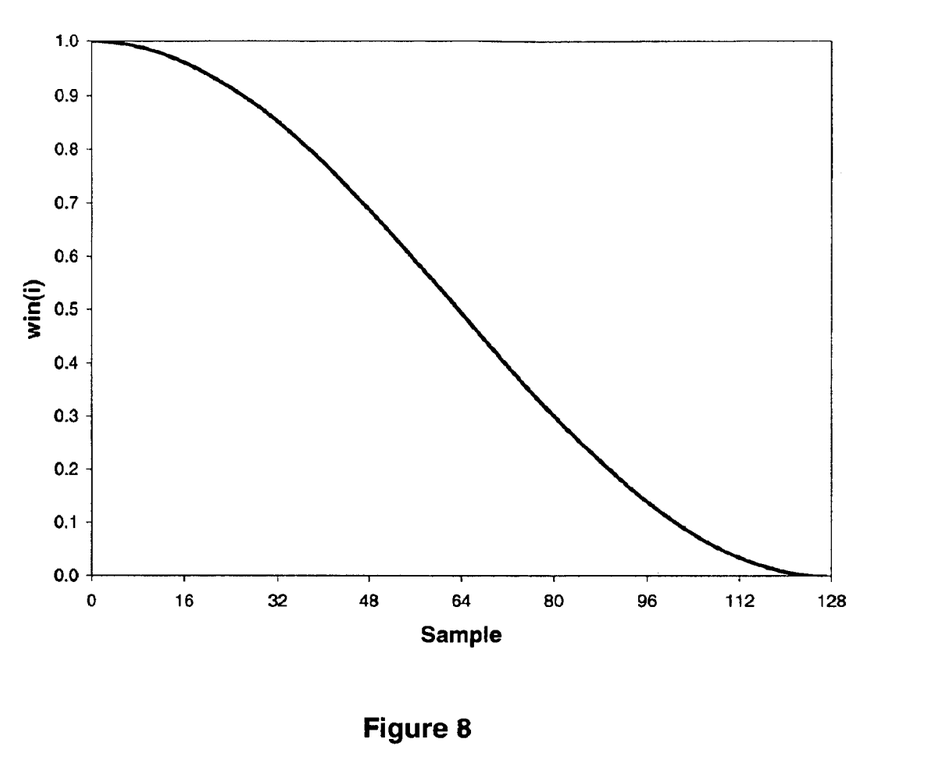
FIG. 8 is a graph of a half Hanning window.

When an epoch from the EEG buffer is used to replace the current EEG epoch, a discontinuity may be created between the first sample of the replacement epoch and the last sample of the previous epoch. In order to transition smoothly from the previous epoch to the replacement epoch, the left edge of the (replacement) current epoch will be adjusted by applying a half Hanning window to the left half of the epoch. The half Hanning window as shown in FIG. 8 is computed as $$win_i = \frac{1}{2} + \frac{1}{2}\cos\left(\frac{\pi \cdot i}{\frac{N}{2}-1}\right)$$

where N is the number of samples in the EEG epoch and the sample number i=0, 1, 2, . . . (N/2)−1.

The half Hanning window ranges from 0 to 1 as it approaches the middle of the epoch. As a result, the first value in the adjusted epoch will be equal to the last value of the previous epoch. The right half of the adjusted epoch will be identical to the original signal. Note that $win_0=1$ and $win_{N/2-1}=0$.

As a first step, the replacement epoch is copied to a temporary output buffer. $SmoothedData_i = NewData_i$
where i=0, 1, 2, . . . N−1
NewData [ ] is the replacement epoch
SmoothedData [ ] is epoch to be output The half Hanning window is used to smooth the left half of the replacement EEG epoch so that it transitions smoothly between the last value in the previous EEG epoch and the middle of the replacement epoch.

$$SmoothedData_i = \left(win_{\frac{N}{2}-i-1} \cdot (SmoothedData_i - PreviousData_{N-1})\right) + PreviousData_{N-1}$$

where $i = 0, 1, 2, \ldots N/2 - 1$ $PreviousData_{N-1}$ is the last value in the previous epoch;

The smoothed epoch in the temporary buffer SmoothedData is then output as the current epoch.

While the foregoing invention has been described with reference to its preferred embodiments, various alterations and modifications will occur to those skilled in the art. All such variations and modifications are intended to fall within the scope of the appended claims.

What is claimed is:

1. A method of removing radio frequency noise in sampled biopotential signals comprising the steps of:
   dividing the biopotential signals into epochs of at least two samples of biopotential signals;
   analyzing each of said epochs to detect whether each of said analyzed epochs of the biopotential signal contains radio frequency noise;
   removing from the biopotential signal each entire epoch that contains radio frequency noise and replacing each of said epochs removed from said biopotential signal with other epochs of the actual detected biopotential signal that do not include radio frequency noise.

2. The method of removing radio frequency noise in biopotential signals of claim 1 wherein said step of analyzing said epochs comprises analyzing said epochs with a hardware detection circuit.

3. The method of removing radio frequency noise in biopotential signals of claim 1 wherein said step of analyzing said epochs comprises analyzing said epochs for changes in the root mean square power of the epoch that are characteristic of high frequency noise.

4. The method of removing radio frequency noise in biopotential signals of claim 1 wherein said step of analyzing said epochs comprises analyzing said epochs for changes in the slew rate of said epochs.

5. The method of removing radio frequency noise in biopotential signals of claim 1 wherein said step of analyzing said epochs comprises
   analyzing said epochs with a hardware detection circuit; and
   analyzing said epochs for changes in the root mean square power of the epoch that are characteristic of high frequency noise.

6. The method of removing radio frequency noise in biopotential signals of claim 1 wherein said step of analyzing said epochs comprises
   analyzing said epochs with a hardware detection circuit; and
   analyzing said epochs for changes in the slew rate of said epochs.

7. The method of removing radio frequency noise in biopotential signals of claim 1 wherein said step of removing said epochs that contain radio frequency noise comprises the steps of:
   maintaining a buffer of the most recent epochs that do not contain radio frequency noise;
   replacing an epoch containing radio frequency noise with an epoch from said buffer that does not contain radio frequency noise.

8. The method of removing radio frequency noise in biopotential signals of claim 7 further comprising the step of adjusting an edge on an epoch used as a replacement epoch so that a first value of each epoch used to replace a removed epoch is equal to a last value of a previous epoch.

9. The method for removing radio frequency noise in sampled biopotential signals of claim 1 wherein said step of analyzing each of said epochs comprises analyzing said epochs for changes in spectral power distribution of the epoch.

10. A system for detecting the presence of radio frequency noise in sampled biopotential signals comprising:

a radio frequency noise detection circuit that analyzes the biopotential signal on an epoch-by-epoch basis to determine if any such epoch contains radio frequency noise wherein each of said epochs includes at least two samples of biopotential signals;

a processor for independently examining said epochs of the biopotential signal to determine if said epochs contain radio frequency noise and for modifying the biopotential signal by removing each entire epoch in the biopotential signal that contains radio frequency noise and replacing each said removed epoch with an epoch of the actual detected biopotential signal that does not contain radio frequency noise.

11. The system for detecting the presence of radio frequency noise in biopotential signals of claim 10 wherein said radio frequency noise detection circuit comprises:

a first stage transistor coupled to a patient lead through which the biopotential signal is obtained;

a second stage transistor coupled to said first stage transistor;

wherein said first stage transistor is normally on thereby keeping said second stage transistor off, and when current through the patient lead exceeds a base bias current said first stage transistor turns off and said second stage transistor turns on indicating the presence of radio frequency noise.

12. The system for detecting the presence of radio frequency noise in biopotential signals of claim 10 wherein said processor analyzes said epochs for changes in the root mean square power of the epoch that are characteristic of high frequency noise.

13. The system for detecting the presence of radio frequency noise in biopotential signals of claim 10 wherein said processor analyzes said epochs for changes in the slew rate of said epochs.

14. The system for detecting the presence of radio frequency noise in biopotential signals of claim 10 further comprising a buffer of the most recent epochs that do not contain radio frequency noise; and wherein said processor replaces an epoch containing radio frequency noise with an epoch from said buffer that does not contain radio frequency noise.

15. The system for detecting the presence of radio frequency noise in biopotential signals of claim 10 wherein said processor adjusts an edge on an epoch used as a replacement epoch so that a first value of each epoch used to replace a removed epoch is equal to a last value of a previous epoch.

16. A system for detecting the presence of radio frequency noise in biopotential signals comprising:

a radio frequency noise detection circuit that analyzes the biopotential signal on an epoch-by-epoch basis to determine if any such epoch contains radio frequency noise;

a processor for independently examining changes in the spectral power distribution of said epochs of the biopotential signal to determine if said epochs contain radio frequency noise and for modifying the biopotential signal by removing each entire epochs in the biopotential signal that contain radio frequency noise and replacing said removed epochs with epochs that do not contain radio frequency noise.

* * * * *